(12) United States Patent
Meerpoel et al.

(10) Patent No.: US 8,258,304 B2
(45) Date of Patent: *Sep. 4, 2012

(54) N-ARYL PIPERIDINE SUBSTITUTED BIPHENYLCARBOXAMIDES

(75) Inventors: Lieven Meerpoel, Beerse (BE); Leo Jacobus Jozef Backx, Arendonk (BE); Peter Walter Maria Roevens, Malle (BE)

(73) Assignee: Janssen Pharmaceutica N.V., Beerse (BE)

( * ) Notice: Subject to any disclaimer, the term of this patent is extended or adjusted under 35 U.S.C. 154(b) by 610 days.

This patent is subject to a terminal disclaimer.

(21) Appl. No.: 12/351,385

(22) Filed: Jan. 9, 2009

(65) Prior Publication Data

US 2009/0156623 A1 Jun. 18, 2009

Related U.S. Application Data

(63) Continuation of application No. 10/524,051, filed as application No. PCT/EP03/08694 on Aug. 5, 2003, now abandoned.

(30) Foreign Application Priority Data

Aug. 12, 2002 (EP) .................................... 02078309

(51) Int. Cl.
*A61K 31/454* (2006.01)
*A61K 31/451* (2006.01)
*C07D 211/62* (2006.01)
*C07D 213/75* (2006.01)

(52) U.S. Cl. ........ 546/194; 514/318; 514/330; 514/331; 546/225; 546/227; 546/233; 546/234; 546/235

(58) Field of Classification Search .................. 514/333, 514/318, 330, 331; 546/194, 225, 227, 233, 546/234, 235
See application file for complete search history.

(56) References Cited

U.S. PATENT DOCUMENTS

| | | | |
|---|---|---|---|
| 4,231,938 A | 11/1980 | Monaghan et al. | |
| 4,346,227 A | 8/1982 | Terahara et al. | |
| 4,444,784 A | 4/1984 | Hoffman et al. | |
| 4,647,576 A | 3/1987 | Hoefle et al. | |
| 4,739,073 A | 4/1988 | Kathawala | |
| 4,847,271 A | 7/1989 | Chabala et al. | |
| 5,041,432 A | 8/1991 | Gaylor et al. | |
| 5,064,856 A | 11/1991 | Garrity et al. | |
| 5,120,729 A | 6/1992 | Chabala et al. | |
| 5,510,379 A | 4/1996 | Lee et al. | |
| 5,512,548 A | 4/1996 | Kushwaha et al. | |
| 7,135,586 B2 | 11/2006 | Meerpoel et al. | |
| 7,244,848 B2 | 7/2007 | Meerpoel et al. | |

FOREIGN PATENT DOCUMENTS

| | | |
|---|---|---|
| EP | 0491226 B1 | 8/1996 |
| EP | 0645377 B1 | 8/1997 |
| EP | 0645378 B1 | 8/2000 |
| EP | 0567026 B1 | 3/2003 |
| WO | WO 96/10559 A1 | 4/1996 |
| WO | WO 96/26948 A1 | 9/1996 |
| WO | WO 00/32582 A1 | 6/2000 |
| WO | WO 01/96327 A1 | 12/2001 |
| WO | WO 01/97810 A2 | 12/2001 |
| WO | WO 02/20501 A2 | 3/2002 |
| WO | WO 02/081460 A1 | 10/2002 |
| WO | WO 03048121 A1 * | 6/2003 |

OTHER PUBLICATIONS

Magnin, D. R. et al. "Microsomal Triglyceride Transfer Protein Inhibitors: Discovery and Synthesis of Alkyl Phosphonates as Potent MTP Inhibitors and Cholesterol Lowering Agents" Bioorganic & Medicinal Chemistry Letters 2003, 13, 1337-1340.*
Ksander et al. "Diaminoindanes as Microsomal Triglyceride Transfer Protein Inhibitors" Journal of Medicinal Chemistry, 2001, 44, 4677-4687.*
Philippe Costet "Molecular pathways and agents for lowering LDL-cholesterol in addition to statins" Pharmacology & Therapeutics 126 (2010) 263-278.*
Atillakos et. al. "Thyroid dysfunction associated with increased low-density lipoprotein cholesterol in epileptic children treated with carbamazepine monotherapy: A causal relationship?" European Journal of Paediatric Neurology, vol. 11, Issue 6, Nov. 2007, 358-361.*
PCT International Search Report dated Oct. 6, 2003 for PCT Application. No. PCT/EP03/08694 which relates to U.S. Patent Application filed herewith.
Sharp et al., "Cloning and Gene Defects in Microsomal Triglyceride Transfer Protein Associated with Abetalipoproteinaemia.", Nature, 1993, Vo. 365, pp. 65-69.
"Known Fluoronitrodiazines", cited in U.S. Appl. No. 10/524,051(Parent).
Dorwald, F.A., Side Reactions in Organic Synthesis, 2005, Wiley: VCH, Weinheim p. IX of Preface, p. 1-15, p. 41.

(Continued)

Primary Examiner — David K O Dell

(57) ABSTRACT

N-aryl piperidine substituted biphenylcarboxamides compounds of formula (I)

(I)

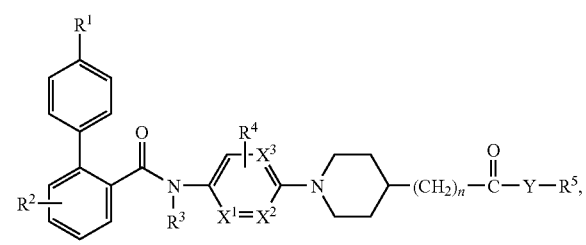

methods for preparing such compounds, pharmaceutical compositions comprising said compounds as well as the use of said compounds as a medicine for the treatment of hyperlipidemia, obesity and type II diabetes.

17 Claims, No Drawings

OTHER PUBLICATIONS

Martin et al., "Do Structurally Similar Molecules Have Similar Biological Activity?", J.Med.Chem, 2002, vol. 45, pp. 4350-4358.

Lunxian, Y., "Synthesis of new calcineurin inhibitors via Pd catalyzed cross-coupling reactions.", Dissertation, 2005, Humboldt-Universität zu Berlin.

Magin et al., "Microsomal Triglyceride Transfer Protein Inhibitors: Discovery and Synthesis of Alkyl Phosphonates as Potent MPT Inhibitors and Cholestrerol Lowering Agents.", Bioorganic & Medicinal Chemistry Letters, 2003, vol. 13, pp. 1337-1340.

Willoughby et al., "Solid Phase Synthesis of Aryl Amines.", Tetrahedron Letters, 1996, pp. 7181-7184, 37(40), Elsevier Science Ltd.

Chan et al., "New N- and O-Arylations with Phenylboronic Acids and Cupric Acetate.", Tetrahedron Letters, 1998, vol. 39, pp. 2933-1936, Elsevier Science Ltd.

Wolfe et al., "An Improved Catalyst System for Aromatic Carbon-Nitrogen Bond Formation: The Possible Involvement of Bis(Phosphine) Palladium Complexes as Key Intermediates.", J. Am.Chem. Soc., 1996, vol. 118, pp. 7215-7216.

Qureshi et al., "3-Hydroxy-3-methylglutaryl-CoA reductase from yeast.", Methods of Enzymology, 1981, vol. 71, pp. 455-509.

Miziorko, H.M., "3-Hydroxy-3-methylglutaryl-CoA synthase from chicken liver.", Methods of Enzymology, 1985, vol. 110, pp. 19-26.

Agnew, W.S., "Squalene synthetase.", Methods of Enzymology, 1985, vol. 110, pp. 359-373.

Mercer, E.I., "Inhibitors of sterol biosynthesis and their applications.", Progress in Lipid Research, 1993, vol. 32(4), pp. 357-416.

Kim et al., "Inhibition of Cholesteryl Ester Transfer Protein by Rosenonolactone Derivatives.", J.Antibioti., 1996, vol. 49(8), pp. 815-816.

Pietzonka et al., "Phosphonate-containing analogs of cholesteryl ester as novel inhibitors of cholesteryl ester transfer protein.", Bioorg. Med. Chem. Lett., 1996, vol. 6(16), pp. 1951-1954.

Heider et al., "Role of acyl CoA:cholesterol acyltransferase in cholesterol absorption and its inhibition by 57-118 in the rabbit.", Journal of Lipid Research, 1983, vol. 24, pp. 1127-1134.

Wetterau et al, "Purification and characterization of microsomal triglyceride and cholesteryl ester transfer protein from bovine liver microsomes.", Chemistry and Physics of Lipids, 1985, vol. 38, pp. 205-222.

Albericio, et al., "Coupling Methods: Solid Phase Formation of Amide and Ester Bonds.", *Solid Phase Synthesis: A Practical Guide*, Marcel Dekker, Inc., 2000 (ISBN: 0-8247-0359-6) pp. 306-319.

Taylor et al., "Use of Oxygenated Stenols to Probe the Regulation of 3-Hydroxy-3-methylglutaryl-CoA Reductase and Sterologenesis.", Methods in Enzymology, 1985, pp. 9-19, vol. 110, Academic Press.

\* cited by examiner

N-ARYL PIPERIDINE SUBSTITUTED BIPHENYLCARBOXAMIDES

CROSS REFERENCE TO RELATED APPLICATIONS

This application is a continuation application of U.S. Ser. No. 10/524,051, filed Feb. 8, 2005 now abandoned, the disclosure of which is hereby incorporated by reference in its entirety, which is the U.S. national stage of and claims priority to Application No. PCT/EP2003/008694, filed Aug. 5, 2003, which application claims priority from EP 02078309.8, filed Aug. 12, 2002.

The present invention is concerned with novel N-aryl piperidine substituted biphenylcarboxamide compounds having apolipoprotein B inhibiting activity and concomitant lipid lowering activity. The invention further relates to methods for preparing such compounds, pharmaceutical compositions comprising said compounds as well as the use of said compounds as a medicine for the treatment of hyperlipidemia, obesity and type II diabetes.

Obesity is the cause of a myriad of serious health problems like the adult onset of diabetes and heart disease. In addition, the loss of weight is getting an obsession among an increasing proportion of the human population.

The causal relationship between hypercholesterolemia, particularly that associated with increased plasma concentrations of low density lipoproteins (hereinafter referred as LDL) and very low density lipoproteins (hereinafter referred as VLDL), and premature atherosclerosis and/or cardiovascular disease is now widely recognized. However, a limited number of drugs are presently available for the treatment of hyperlipidemia.

Drugs primarily used for the management of hyperlipidemia include bile acid sequestrant resins such as cholestyramine and colestipol, fibric acid derivatives such as bezafibrate, clofibrate, fenofibrate, ciprofibrate and gemfibrozil, nicotinic acid and cholesterol synthesis inhibitors such as HMG Co-enzyme-A reductase inhibitors. There still remains a need for new lipid lowering agents with improved efficiency and/or acting via other mechanisms than the above mentioned drugs.

Plasma lipoproteins are water-soluble complexes of high molecular weight formed from lipids (cholesterol, triglyceride, phospholipids) and apolipoproteins. Five major classes of lipoproteins that differ in the proportion of lipids and the type of apolipoprotein, all having their origin in the liver and/or the intestine, have been defined according to their density (as measured by ultracentrifugation). They include LDL, VLDL, intermediate density lipoproteins (hereinafter referred as IDL), high density lipoproteins (hereinafter referred as HDL) and chylomicrons. Ten major human plasma apolipoproteins have been identified. VLDL, which is secreted by the liver and contains apolipoprotein B (hereinafter referred as Apo-B), undergoes degradation to LDL which transports 60 to 70% of the total serum cholesterol. Apo-B is also the main protein component of LDL. Increased LDL-cholesterol in serum, due to oversynthesis or decreased metabolism, is causally related to atherosclerosis. In contrast high density lipoproteins (hereinafter referred as HDL), which contain apolipoprotein A1, have a protective effect and are inversely correlated with the risk of a coronary heart disease. The HDL/LDL ratio is thus a convenient method of assessing the atherogenic potential of an individual's plasma lipid profile.

The two isoforms of apolipoprotein (apo) B, apo B-48 and apo B-100, are important proteins in human lipoprotein metabolism. Apo B-48, so named because it appears to be about 48% the size of apo B-100 on sodium dodecyl sulfate-polyacrylamide gels, is synthesized by the intestine in humans. Apo B-48 is necessary for the assembly of chylomicrons and therefore has an obligatory role in the intestinal absorption of dietary fats. Apo B-100, which is produced in the liver in humans, is required for the synthesis and secretion of VLDL. LDL, which contain about ⅔ of the cholesterol in human plasma, are metabolic products of VLDL. Apo B-100 is virtually the only protein component of LDL. Elevated concentrations of apo B-100 and LDL cholesterol in plasma are recognized risk factors for developing atherosclerotic coronary artery disease.

A large number of genetic and acquired diseases can result in hyperlipidemia. They can be classified into primary and secondary hyperlipidemic states. The most common causes of the secondary hyperlipidemias are diabetes mellitus, alcohol abuse, drugs, hypothyroidism, chronic renal failure, nephrotic syndrome, cholestasis and bulimia. Primary hyperlipidemias have also been classified into common hypercholesterolaemia, familial combined hyperlipidaemia, familial hypercholesterolaemia, remnant hyperlipidaemia, chylomicronaemia syndrome and familial hyper-triglyceridaemia.

Microsomal triglyceride transfer protein (hereinafter referred as MTP) is known to catalyze the transport of triglyceride and cholesteryl ester by preference to phospholipids such as phosphatidylcholine. It was demonstrated by D. Sharp et al., Nature (1993) 365:65 that the defect causing abetalipoproteinemia is in the MTP gene. This indicates that MTP is required for the synthesis of Apo B-containing lipoproteins such as VLDL, the precursor to LDL. It therefore follows that an MTP inhibitor would inhibit the synthesis of VLDL and LDL, thereby lowering levels of VLDL, LDL, cholesterol and triglyceride in humans.

One of the goals of the present invention is to provide an improved treatment for patients suffering from obesity or atherosclerosis, especially coronary atherosclerosis and more generally from disorders which are related to atherosclerosis, such as ischaemic heart disease, peripheral vascular disease and cerebral vascular disease. Another goal of the present invention is to cause regression of atherosclerosis and inhibit its clinical consequences, particularly morbidity and mortality.

MTP inhibitors have been disclosed in WO-00/32582, WO-01/96327 and WO-02/20501.

The present invention is based on the unexpected discovery that a class of novel N-aryl piperidine substituted biphenylcarboxamide compounds is acting as selective MTP inhibitors, i.e. is able to selectively block MTP at the level of the gut wall in mammals, and is therefore a promising candidate as a medicine, namely for the treatment of hyperlipidemia. The present invention additionally provides several methods for preparing such N-aryl piperidine substituted biphenylcarboxamide compounds, as well as pharmaceutical compositions including such compounds. Furthermore, the invention provides a certain number of novel compounds which are useful intermediates for the preparation of the therapeutically active N-aryl piperidine substituted biphenyl-carboxamide compounds, as well as methods for preparing such intermediates. Finally, the invention provides a method of treatment of a condition selected from atherosclerosis, pancreatitis, obesity, hypercholesterolemia, hypertriglyceridemia, hyperlipidemia, diabetes and type II diabetes, comprising administering a therapeutically active biphenylcarboxamide compound to a mammal.

The present invention relates to a family of novel compounds of formula (I)

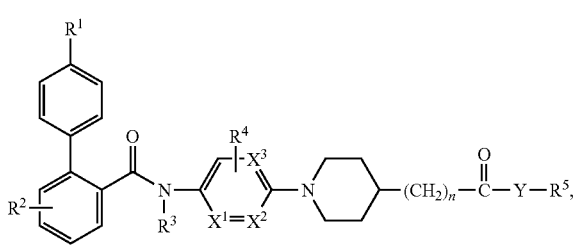

the N-oxides, the pharmaceutically acceptable acid addition salts and the stereochemically isomeric forms thereof, wherein
$R^1$ is hydrogen, $C_{1-4}$alkyl, halo, or polyhalo$C_{1-4}$alkyl;
$R^2$ is hydrogen, $C_{1-4}$alkyl, halo, or polyhalo$C_{1-4}$alkyl;
$R^3$ is hydrogen or $C_{1-4}$alkyl;
$R^4$ is hydrogen, $C_{1-4}$alkyl, or halo;
n is an integer zero or 1;
$X^1$ and $X^2$ are either both carbon, or when one of $X^1$ or $X^2$ is nitrogen, than the other
$X^1$ or $X^2$ is carbon;
$X^3$ is carbon, or nitrogen provided that only one of $X^1$ or $X^2$ is nitrogen;
Y is O or $NR^6$ wherein $R^6$ is hydrogen or $C_{1-4}$alkyl; and
$R^5$ is hydrogen; $C_{1-6}$alkyl optionally substituted with $C_{1-4}$alkyloxy, cyano, polyhalo$C_{1-4}$alkyl, or aryl; $C_{2-6}$alkenyl optionally substituted with aryl; $C_{3-6}$alkynyl optionally substituted with aryl; aryl or heteroaryl;
aryl is phenyl; phenyl substituted with one, two or three substituents each independently selected from nitro, azido, cyano, halo, hydroxy, $C_{1-6}$alkyl, $C_{3-6}$cycloalkyl, $C_{1-4}$alkyloxy, polyhalo$C_{1-6}$alkyl, amino, mono- or di($C_{1-6}$alkyl) amino;
heteroaryl is pyridinyl, pyrazinyl, pyrimidinyl, pyridazinyl, triazinyl, triazolyl, imidazolyl, pyrazolyl, thiazolyl, isothiazolyl, oxazolyl, pyrrolyl, furanyl, or thienyl; and optionally substituted with one, two or three substituents each independently selected from nitro, azido, cyano, halo, hydroxy, $C_{1-6}$alkyl, $C_{3-6}$cycloalkyl, $C_{1-4}$alkyloxy, polyhalo$C_{1-4}$alkyl, amino, mono- or di($C_{1-6}$alkyl)amino.

Unless otherwise stated, as used in the foregoing definitions and hereinafter:
halo is generic to fluoro, chloro, bromo and iodo;
$C_{1-4}$alkyl defines straight and branched chain saturated hydrocarbon radicals having from 1 to 4 carbon atoms such as, for example, methyl, ethyl, propyl, n-butyl, 1-methylethyl, 2-methylpropyl, 1,1-dimethylethyl and the like;
$C_{1-6}$alkyl is meant to include $C_{1-4}$alkyl (as hereinabove defined) and the higher homologues thereof having 5 or 6 carbon atoms, such as for instance 2-methylbutyl, n-pentyl, dimethylpropyl, n-hexyl, 2-methylpentyl, 3-methylpentyl and the like;
polyhalo$C_{1-4}$alkyl is defined as polyhalosubstituted $C_{1-4}$alkyl, in particular $C_{1-4}$alkyl (as hereinabove defined) substituted with 2 to 6 halogen atoms such as difluoromethyl, trifluoromethyl, trifluoroethyl, and the like;
$C_{2-6}$alkenyl defines straight and branched chain unsaturated hydrocarbon radicals having from 2 to 6 carbon atoms, such as ethenyl, propenyl, butenyl, pentenyl or hexenyl;
$C_{3-6}$alkynyl defines straight and branched chain hydrocarbon radicals containing one triple bond and having from 3 to 6 carbon atoms such as, for example, 2-propynyl, 3-butynyl, 2-butynyl, 2-pentynyl, 3-pentynyl, 3-methyl-2-butynyl, 3-hexynyl, 2-hexynyl and the like;
$C_{1-4}$alkylamino defines primary amino radicals having from 1 to 6 carbon atoms such as, for example, methylamino, ethylamino, propylamino, isopropylamino, butylamino, isobutylamino and the like;
di($C_{1-16}$alkyl)amino defines secondary amino radicals having from 1 to 6 carbon atoms such as, for example, dimethylamino, diethylamino, dipropylamino, diisopropylamino, N-methyl-N'-ethylamino, N-ethyl-N'-propylamino and the like.

The pharmaceutically acceptable acid addition salts as mentioned hereinabove are meant to comprise the therapeutically active non-toxic acid addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The term addition salt as used hereinabove also comprises the solvates which the compounds of formula (I) as well as the salts thereof, are able to form. Such solvates are for example hydrates, alcoholates and the like.

The N-oxide forms of the compounds of formula (I), which may be prepared in art-known manners, are meant to comprise those compounds of formula (I) wherein a nitrogen atom is oxidized to the N-oxide.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Unless otherwise mentioned or indicated, the chemical designation of compounds denotes the mixture of all possible stereoisomeric forms, said mixtures containing all diastereomers and enantiomers of the basic molecular structure. The same applies to the intermediates as described herein, used to prepare end products of formula (I).

The terms cis and trans are used herein in accordance with Chemical Abstracts nomenclature and refer to the position of the substituents on a ring moiety.

The absolute stereochemical configuration of the compounds of formula (I) and of the intermediates used in their preparation may easily be determined by those skilled in the art while using well-known methods such as, for example, X-ray diffraction.

Furthermore, some compounds of formula (I) and some of the intermediates used in their preparation may exhibit polymorphism. It is to be understood that the present invention encompasses any polymorphic forms possessing properties useful in the treatment of the conditions noted hereinabove.

A group of interesting compounds consists of those compounds of formula (I) wherein one or more of the following restrictions apply:
  a) $R^1$ is tert-butyl or trifluoromethyl;
  b) $R^2$ is hydrogen or $C_{1-4}$alkyl;
  c) $R^3$ is hydrogen;
  d) $R^4$ is hydrogen;
  e) $R^5$ is $C_{1-4}$alkyl or $C_{1-4}$alkyl substituted with phenyl.

A first particular group of compounds are those compounds of formula (I) wherein $X^1$, $X^2$ and $X^3$ are carbon.

A second particular group of compounds are those compounds of formula (I) wherein $X^1$ is carbon, $X^2$ is nitrogen, and $X^3$ is carbon.

A third particular group of compounds are those compounds of formula (I) wherein $X^1$ is nitrogen, $X^2$ is carbon, and $X^3$ is carbon.

A fourth particular group of compounds are those compounds of formula (I) wherein $X^1$ is carbon, $X^2$ is nitrogen, and $X^3$ is nitrogen.

A fifth particular group of compounds are those compounds of formula (I) wherein n is the integer zero.

A sixth particular group of compounds are those compounds of formula (I) wherein n is the integer 1.

A first preferred group of compounds are those compounds of formula (I) wherein $R^1$ is $C_{1-4}$alkyl, or trifluoromethyl; $R^2$ is hydrogen or $C_{1-4}$alkyl; $R^3$ is hydrogen; $R^4$ is hydrogen; $R^5$ is $C_{1-4}$alkyl or $C_{1-4}$alkyl substituted with phenyl; n is the integer zero; and $X^1$, $X^2$ and $X^3$ are carbon.

A second preferred group of compounds are those compounds of formula (I) wherein $R^1$ is $C_{1-4}$alkyl, or trifluoromethyl; $R^2$ is hydrogen or $C_{1-4}$alkyl; $R^3$ is hydrogen; $R^4$ is hydrogen; $R^5$ is $C_{1-4}$alkyl or $C_{1-4}$alkyl substituted with phenyl; n is the integer 1; and $X^1$, $X^2$ and $X^3$ are carbon.

A third preferred group of compounds are those compounds of formula (I) wherein $R^1$ is $C_{1-4}$alkyl, or trifluoromethyl; $R^2$ is hydrogen or $C_{1-4}$alkyl; $R^3$ is hydrogen; $R^4$ is hydrogen; $R^5$ is $C_{1-4}$alkyl or $C_{1-4}$alkyl substituted with phenyl; n is the integer zero; $X^3$ is carbon and $X^1$ or $X^2$ is nitrogen, and the other $X^1$ or $X^2$ is carbon.

A fourth preferred group of compounds are those compounds of formula (I) wherein $R^1$ is $C_{1-4}$alkyl, or trifluoromethyl; $R^2$ is hydrogen or $C_{1-4}$alkyl; $R^3$ is hydrogen; $R^4$ is hydrogen; $R^5$ is $C_{1-4}$alkyl or $C_{1-4}$alkyl substituted with phenyl; n is the integer 1; $X^3$ is carbon and $X^1$ or $X^2$ is nitrogen, and the other $X^1$ or $X^2$ is carbon.

A first more preferred group of compounds are one of the preferred groups of compounds wherein Y is O.

A second more preferred group of compounds are one of the preferred groups of compounds wherein Y is NH.

A first process for preparing compounds of formula (I) is a process wherein an intermediate of formula (II)

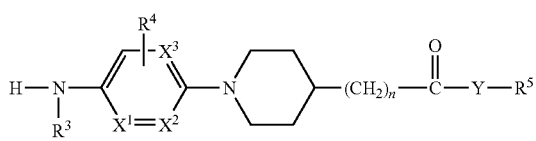

(II)

wherein $R^3$, $R^4$, $R^5$, n, Y, $X^1$, $X^2$ and $X^3$ are as defined in formula (I), is reacted with a biphenylcarboxylic acid or halide having the formula (III),

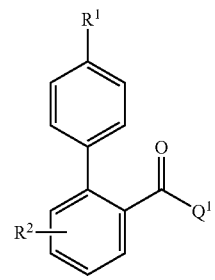

(III)

wherein $R^1$ and $R^2$ are as defined in formula (I) and $Q^1$ is selected from hydroxy and halo, in at least one reaction-inert solvent and optionally in the presence of a suitable base, the said process further optionally comprising converting a compound of formula (I) into an addition salt thereof, and/or preparing stereochemically isomeric forms thereof. In case $Q^1$ is hydroxy, it may be convenient to activate the biphenylcarboxylic acid of formula (III) by adding an effective amount of a reaction promoter. Non-limiting examples of such reaction promoters include carbonyldiimidazole, diimides such as N,N'-dicyclohexylcarbodiimide (DCC) or 1-ethyl-3-(3'-dimethylaminopropyl)-carbodiimide (ECC), and functional derivatives thereof. For this type of acylation procedure, it is preferred to use a polar aprotic solvent such as, for instance, dichloromethane. Suitable bases for carrying out this first process include tertiary amines such as triethylamine, triisopropylamine and the like. Suitable temperatures for carrying out the first process of the invention typically range from about 20° C. to about 140° C., depending on the particular solvent used, and will most often be the boiling temperature of the said solvent.

A second process for preparing a biphenylcarboxamide compound of the invention is a process wherein an intermediate having the formula (IV)

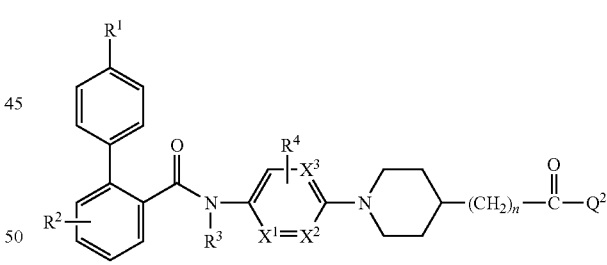

(IV)

wherein $R^1$, $R^2$, $R^3$, $R^4$, n, $X^1$, $X^2$ and $X^3$ are as defined in formula (I) and $Q^2$ is selected from halo and hydroxy, is reacted with an intermediate (V) of the formula $R^5$—Y—H, wherein $R^5$ and Y are as defined in formula (I), in at least one reaction-inert solvent and optionally in the presence of at least one suitable coupling reagent and/or a suitable base, the said process further optionally comprising converting a compound of formula (I) into an addition salt thereof, and/or preparing stereochemically isomeric forms thereof. In case $Q^2$ is hydroxy, it may be convenient to activate the carboxylic acid of formula (IV) by adding an effective amount of a reaction promoter. Non-limiting examples of such reaction promoters include carbonyldiimidazole, diimides such as DCC, ECC, hydroxybenzotriazole, benzotriazol-1-yl-N-oxytris-(dimethylamino)phosphonium hexafluorophosphate (BOP), tetrapyrrolidino-phosphonium hexafluorophosphate, bromotripyrrolidinophosphonium hexafluorophosphate, or a functional derivative thereof, such as disclosed in "Solid-Phase Synthesis: A Practical Guide", edited by Steven A. Kates and Fernando Albericio, Marcel Dekker, Inc., 2000 (ISBN: 0-8247-0359-6) on pages 306 to 319.

A third process for preparing a biphenylcarboxamide compound according to this invention is a process wherein an intermediate having the formula (VI)

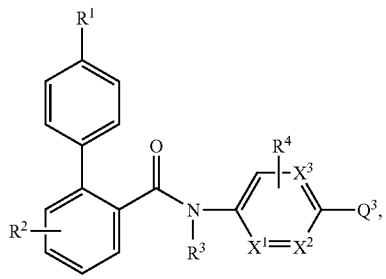

(VI)

wherein $R^1$, $R^2$, $R^3$, $R^4$, $X^1$, $X^2$ and $X^3$ are as defined in formula (I) and $Q^3$ is selected from halo, $B(OH)_2$, alkylboronates and cyclic analogues thereof, is reacted with a reactant having the formula (VII)

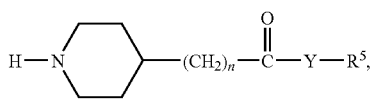

(VII)

wherein n, Y and $R^5$ are as defined in formula (I), in at least one reaction-inert solvent and optionally in the presence of at least one transition metal coupling reagent and/or at least one suitable ligand, the said process further optionally comprising converting a compound of formula (I) into an addition salt thereof, and/or preparing stereochemically isomeric forms thereof. This type of reaction being known in the art as the Buchwald reaction, reference to the applicable metal coupling reagents and/or suitable ligands, e.g. palladium compounds such as palladium tetra(triphenyl-phosphine), tris (dibenzylidene-acetone dipalladium, 2,2'-bis (diphenylphosphino)-1,1'-binaphtyl (BINAP) and the like, may be found for instance in *Tetrahedron Letters*, (1996), 37(40), 7181-7184 and *J. Am. Chem. Soc.*, (1996), 118:7216.

If $Q^3$ is $B(OH)_2$, an alkylboronate or a cyclic analogue thereof, then cupric acetate should be used as the coupling reagent, according to *Tetrahedron Letters*, (1998), 39:2933-6.

Compounds of formula (I-a), defined as compounds of formula (I) wherein Y represent NH and $R^3$ represents hydrogen, can conveniently be prepared using solid phase synthesis techniques as depicted in Scheme 1 below. In general, solid phase synthesis involves reacting an intermediate in a synthesis with a polymer support. This polymer supported intermediate can then be carried on through a number of synthetic steps. After each step, impurities are removed by filtering the resin and washing it numerous times with various solvents. At each step the resin can be split up to react with various intermediates in the next step thus allowing for the synthesis of a large number of compounds. After the last step in the procedure the resin is treated with a reagent or process to cleave the resin from the sample. More detailed explanation of the techniques used in solid phase chemistry are described in for example "Handbook of Combinatorial Chemistry: Drugs, Catalysts, Materials" edited by K. C. Nicolaou, R. Hanko, and W. Hartwig, volumes 1 and 2, Wiley (ISBN: 3-527-30509-2).

Scheme 1:

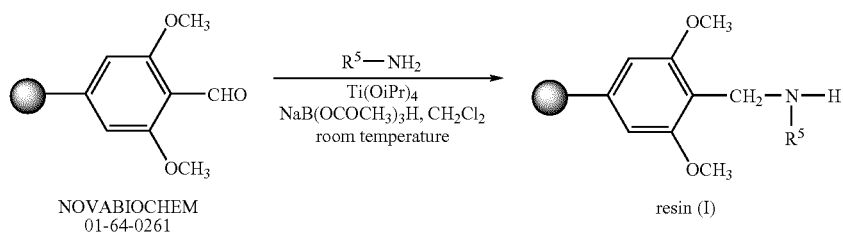

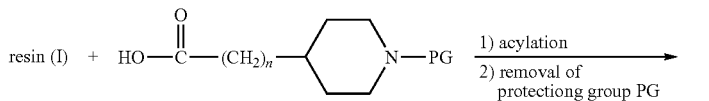

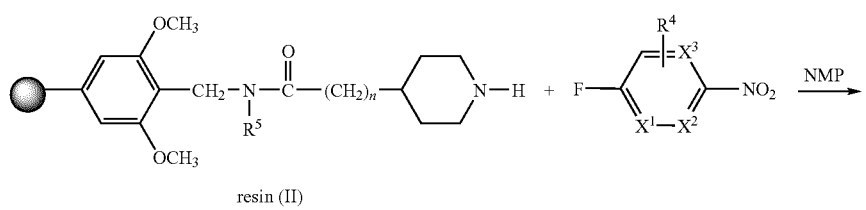

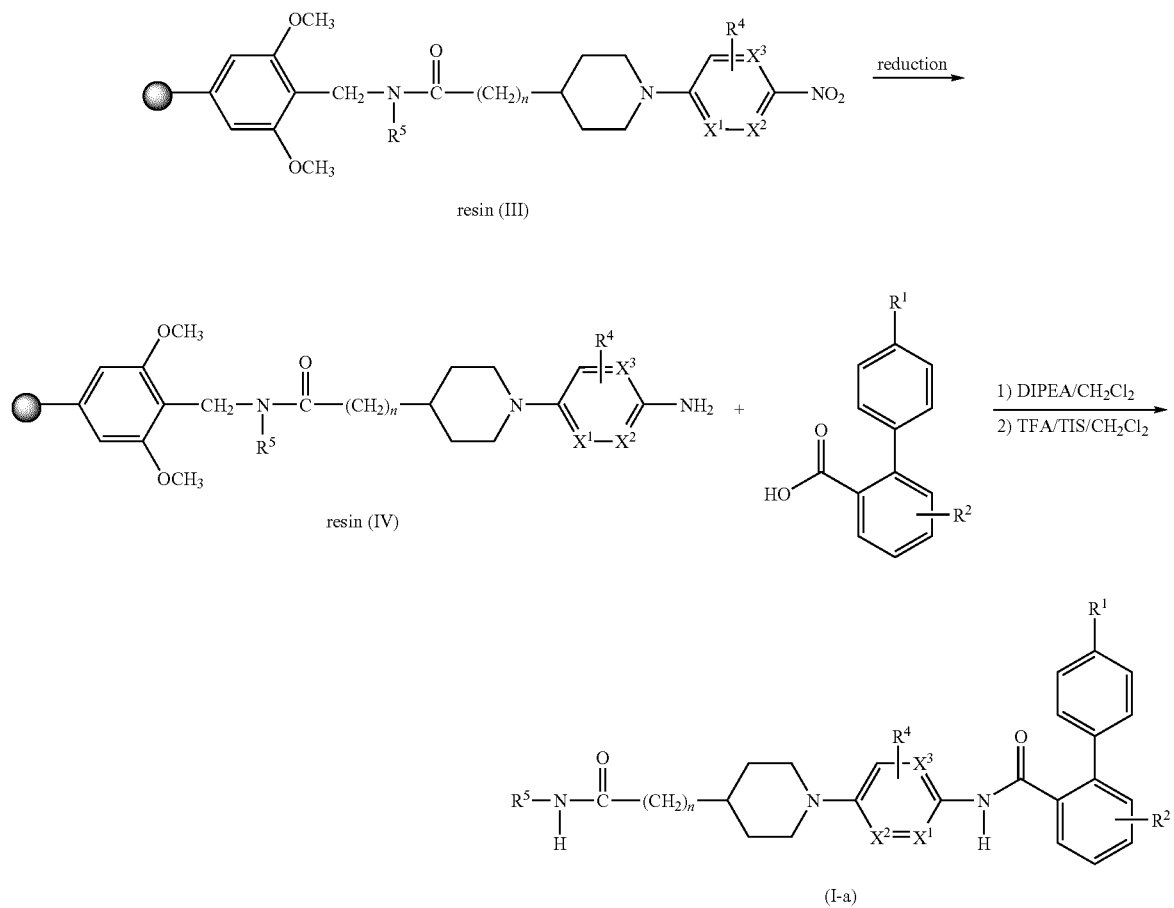

resin (III)

resin (IV)

(I-a)

The abbreviations used in Scheme 1 are explained in the Experimental Part. The substituents $R^1$, $R^2$, $R^3$, $R^4$, $R^4$, $R^5$, n, Y, $X^1$, $X^2$ and $X^3$ are as defined for compounds of formula (I). PG represents a protecting group such as, e.g. $C_{1-6}$alkyloxycarbonyl, phenylmethyloxycarbonyl, t-butoxycarbonyl, 9-fluorenylmethoxycarbonyl (Fmoc) and the like.

Compounds of formula (I-b), defined as compounds of formula (I) wherein $R^3$ represents hydrogen, may be prepared using a solid phase synthesis route as outlined in Scheme 2.

Scheme 2:

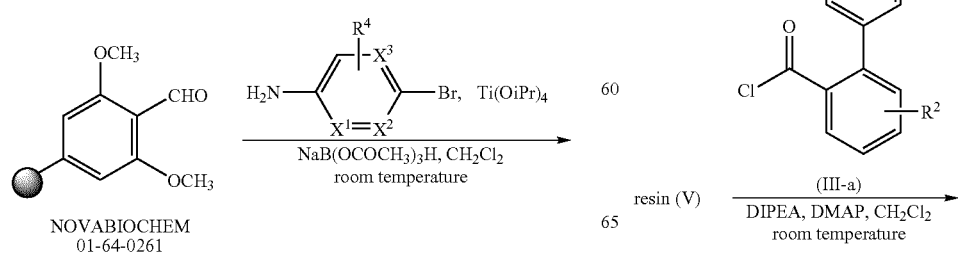

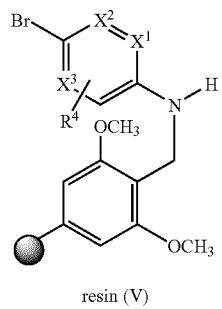

resin (V)

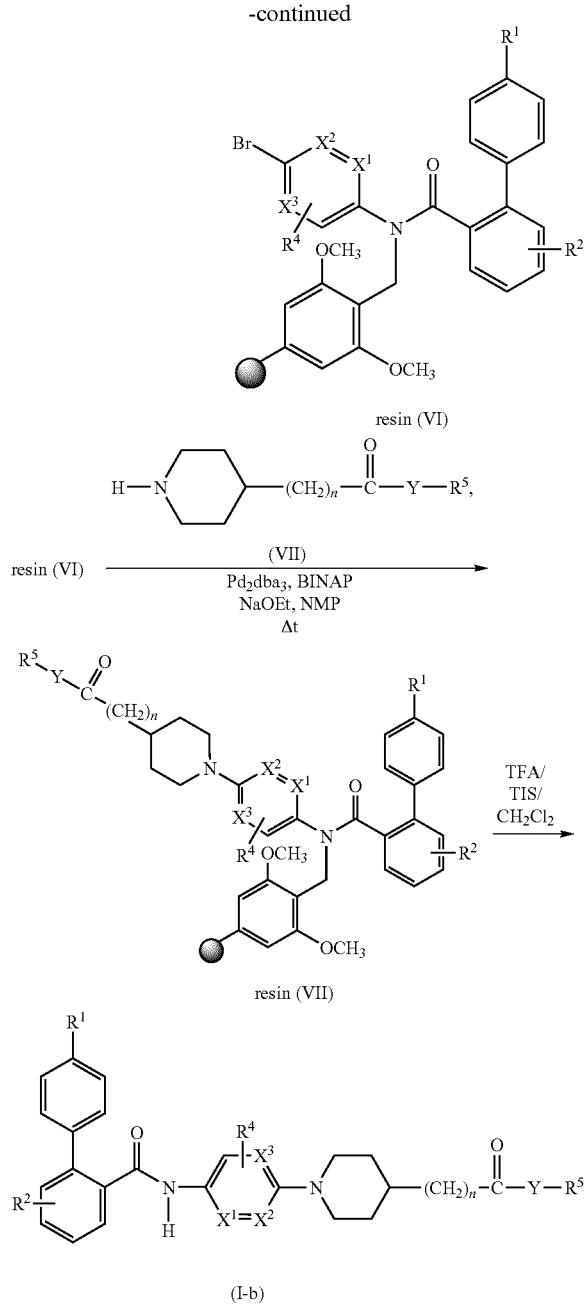

The compounds of formula (I) as prepared in the hereinabove described processes may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The N-aryl piperidine substituted biphenylcarboxamide compounds of formula (I), the N-oxide forms, the pharmaceutically acceptable salts and stereoisomeric forms thereof possess favourable apolipoprotein B inhibiting activity and concomitant lipid lowering activity. Therefore the present compounds are useful as a medicine especially in a method of treating patients suffering from hyperlipidemia, obesity, atherosclerosis or type II diabetes. In particular the present compounds may be used for the manufacture of a medicine for treating disorders caused by an excess of very low density lipoproteins (VLDL) or low density lipoproteins (LDL), and especially disorders caused by the cholesterol associated with said VLDL and LDL.

The principal mechanism of action of the compounds of formula (I) appears to involve inhibition of MTP (microsomial triglyceride transfer protein) activity in hepatocytes and intestinal epithelial cells, resulting in decreased VLDL and chylomicron production, respectively. This is a novel and innovative approach to hyperlipidemia, and is expected to lower LDL-cholesterol and triglycerides through reduced hepatic production of VLDL and intestinal production of chylomicrons.

A large number of genetic and acquired diseases can result in hyperlipidemia. They can be classified into primary and secondary hyperlipidemic states. The most common causes of the secondary hyperlipidemias are diabetes mellitus, alcohol abuse, drugs, hypothyroidism, chronic renal failure, nephrotic syndrome, cholestasis and bulimia. Primary hyperlipidemias are common hypercholesterolaemia, familial combined hyperlipidaemia, familial hypercholesterolaemia, remnant hyperlipidaemia, chylo-micronaemia syndrome, familial hypertriglyceridaemia. The present compounds may also be used to prevent or treat patients suffering from obesitas or from atherosclerosis, especially coronary atherosclerosis and more in general disorders which are related to atherosclerosis, such as ischaemic heart disease, peripheral vascular disease, cerebral vascular disease. The present compounds may cause regression of atherosclerosis and inhibit the clinical consequences of atherosclerosis, particularly morbidity and mortality.

In view of the utility of the compounds of formula (I), it follows that the present invention also provides a method of treating warm-blooded animals, including humans, (generally called herein patients) suffering from disorders caused by an excess of very low density lipoproteins (VLDL) or low density lipoproteins (LDL), and especially disorders caused by the cholesterol associated with said VLDL and LDL. Consequently a method of treatment is provided for relieving patients suffering from conditions, such as, for example, hyperlipidemia, obesity, atherosclerosis or type II diabetes.

Apo B-48, synthesized by the intestine, is necessary for the assembly of chylomicrons and therefore has an obligatory role in the intestinal absorption of dietary fats. The present invention provides biphenylcarboxamide compounds which are acting as selective MTP inhibitors at the level of the gut wall.

Additionally the present invention provides pharmaceutical compositions comprising at least one pharmaceutically acceptable carrier and a therapeutically effective amount of a N-aryl piperidine substituted biphenylcarboxamide compound having the formula (I).

In order to prepare the pharmaceutical compositions of this invention, an effective amount of the particular compound, in base or addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient. Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (I), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage. "Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium laurylsulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, a dihydrochalcone sweetener, monellin, stevioside sucralose (4,1',6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like. Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The N-aryl piperidine substituted biphenylcarboxamide compounds of this invention may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use. The biphenylcarboxamide compounds of this invention may also be formulated in rectal compositions such as suppositories or retention enemas, e.g. containing conventional suppository bases such as cocoa butter and/or other glycerides.

The N-aryl piperidine substituted biphenylcarboxamide compounds of this invention may be used in conjunction with other pharmaceutical agents, in particular the pharmaceutical compositions of the present invention may further comprise at least one additional lipid-lowering agent, thus leading to a so-called combination lipid-lowering therapy. The said additional lipid-lowering agent may be, for instance, a known drug conventionally used for the management of hyperlipidaemia such as e.g. a bile acid sequestrant resin, a fibric acid derivative or nicotinic acid as previously mentioned in the background of the invention. Suitable additional lipid-lowering agents also include other cholesterol biosynthesis inhibitors and cholesterol absorption inhibitors, especially HMG-CoA reductase inhibitors and HMG-CoA synthase inhibitors, HMG-CoA reductase gene expression inhibitors, CETP inhibitors, ACAT inhibitors, squalene synthetase inhibitors and the like.

Any HMG-CoA reductase inhibitor may be used as the second compound in the combination therapy aspect of this invention. The term "HMG-CoA reductase inhibitor" as used herein, unless otherwise stated, refers to a compound which inhibits the biotransformation of hydroxymethylglutaryl-coenzyme A to mevalonic acid as catalyzed by the enzyme HMG-CoA reductase. Such inhibition may be determined readily by one skilled in the art according to standard assays, i.e. Methods of Enzymology (1981) 71:455-509. Exemplary compounds are described e.g. in U.S. Pat. No. 4,231,938 (including lovastatin), U.S. Pat. No. 4,444,784 (including simvastatin), U.S. Pat. No. 4,739,073 (including fluvastatin), U.S. Pat. No. 4,346,227 (including pravastatin), EP-A-491, 226 (including rivastatin) and U.S. Pat. No. 4,647,576 (including atorvastatin).

Any HMG-CoA synthase inhibitor may be used as the second compound in the combination therapy aspect of this invention. The term "HMG-CoA synthase inhibitor" as used herein, unless otherwise stated, refers to a compound which inhibits the biosynthesis of hydroxymethylglutaryl-coenzyme A from acetyl-coenzyme A and acetoacetyl-coenzyme A, catalyzed by the enzyme HMG-CoA synthase. Such inhibition may be determined readily by one skilled in the art according to standard assays, i.e. Methods of Enzymology (1985) 110:19-26. Exemplary compounds are described e.g. in U.S. Pat. No. 5,120,729 relating to beta-lactam derivatives, U.S. Pat. No. 5,064,856 relating to spiro-lactone derivatives and U.S. Pat. No. 4,847,271 relating to oxetane compounds.

Any HMG-CoA reductase gene expression inhibitor may be used as the second compound in the combination therapy aspect of this invention. These agents may be HMG-CoA reductase transcription inhibitors that block the transcription of DNA or translation inhibitors that prevent translation of mRNA coding for HMG-CoA reductase into protein. Such inhibitors may either affect transcription or translation directly or may be biotransformed into compounds having the above-mentioned attributes by one or more enzymes in the cholesterol biosynthetic cascade or may lead to accumulation of a metabolite having the above-mentioned activities. Such regulation may be determined readily by one skilled in the art according to standard assays, i.e. Methods of Enzymology (1985) 110:9-19. Exemplary compounds are described e.g. in U.S. Pat. No. 5,041,432 and E. I. Mercer, *Prog. Lip. Res.* (1993) 32:357-416.

Any CETP inhibitor may be used as the second compound in the combination therapy aspect of this invention. The term "CETP inhibitor" as used herein, unless otherwise stated, refers to a compound which inhibits the cholesteryl ester transfer protein (CETP) mediated transport of various cholesteryl esters and triglycerides from HDL to LDL and VLDL. Exemplary compounds are described e.g. in U.S. Pat. No. 5,512,548, in *J. Antibiot.* (1996) 49(8):815-816 and *Bioorg. Med. Chem. Lett.* (1996) 6:1951-1954.

Any ACAT inhibitor may be used as the second compound in the combination therapy aspect of this invention. The term "ACAT inhibitor" as used herein, unless otherwise stated, refers to a compound which inhibits the intracellular esterification of dietary cholesterol by the enzyme acyl CoA:cholesterol acyltransferase. Such inhibition may be determined readily by one skilled in the art according to standard assays, i.e. the method of Heider et al., *Journal of Lipid Research* (1983) 24:1127. Exemplary compounds are described e.g. in U.S. Pat. No. 5,510,379, in WO 96/26948 and WO 96/10559.

Any squalene synthetase inhibitor may be used as the second compound in the combination therapy aspect of this invention. The term "squalene synthetase inhibitor" as used herein, unless otherwise stated, refers to a compound which inhibits the condensation of two molecules of farnesylpyrophosphate to form squalene, catalyzed by the enzyme squalene synthetase. Such inhibition may be determined readily by one skilled in the art according to standard methods, i.e. Methods of Enzymology (1985) 110:359-373. Exemplary compounds are described e.g. in EP-0,567,026, in EP-0,645,378 and in EP-0,645,377.

Those of skill in the treatment of hyperlipidemia will easily determine the therapeutically effective amount of a biphenylcarboxamide compound of this invention from the test results presented hereinafter. In general it is contemplated that a therapeutically effective dose will be from about 0.001 mg/kg to about 5 mg/kg of body weight, more preferably from about 0.01 mg/kg to about 0.5 mg/kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 350 mg, more particularly from about 1 to about 200 mg, of the active ingredient per unit dosage form.

The exact dosage and frequency of administration depends on the particular biphenylcarboxamide compound of formula (I) used, the particular condition being treated, the severity of the condition being treated, the age, weight and general physical condition of the particular patient as well as the other medication (including the above-mentioned additional lipid-lowering agents), the patient may be taking, as is well known to those skilled in the art. Furthermore, said effective daily amount may be lowered or increased depending on the response of the treated patient and/or depending on the evaluation of the physician prescribing the biphenylcarboxamide compounds of the instant invention. The effective daily amount ranges mentioned hereinabove are therefore only guidelines.

Experimental Part

In the procedures described hereinafter the following abbreviations were used: "DMSO" stands for dimethylsulfoxide, "THF" stands for tetrahydrofuran; "DCM" stands for dichloromethane; "DIPE" stands for diisopropylether; "DMF" means N,N-dimethyl-formamide; "TFFH" stands for tetramethylfluoroformamidinium hexafluorophosphate; "NMP" means N-methyl-2-pyrrolidone and; "DIPEA" means diisopropylethylamine; "TFA" means trifluoroacetic acid; and "TIS" means triisopropylsilane.

A. Synthesis of the Intermediates

Example A.1 a) A mixture of 4-(ethoxycarbonylmethyl)piperidine (0.0222 mol) and 2-chloro-5-nitropyridine (0.0222 mol) in DMSO (40 ml) was stirred in the presence of $Na_2CO_3$ during 2 hours. The reaction mixture was cooled to room temperature and poured into an ice/water mixture. The resulting precipitate was filtered and washed with water. The reaction product was purified by recrystallisation from a mixture of ethyl acetate and hexane, yielding (5'-nitro-3,4,5,6-tetrahydro-2H-[1,2']bipyridinyl-4-yl)-acetic acid ethyl ester (intermediate 1, mp. 99-101° C.).

b) A mixture of intermediate (1) (0.0102 mol) in THF (50 ml) was hydrogenated with palladium on carbon (10%; 0.3 g) as a catalyst for 30 minutes at a temperature of 50° C. After uptake of hydrogen (1 equivalent), the catalyst was filtered off and the filtrate was evaporated, yielding (5'-amino-3,4,5,6-tetrahydro-2H-[1,2']bipyridinyl-4-yl)-acetic acid ethyl ester (intermediate 2).

Example A.2 a) A mixture of 4-(ethoxycarbonylmethyl)piperidine (0.011 mol) and 1-fluoro-4-nitrobenzene (0.011 mol) in DMSO (20 ml) was stirred in the presence of $Na_2CO_3$ (0.044 mol) during 2 hours at a temperature of 60° C. The reaction mixture was cooled to room temperature and poured into an ice/water mixture. The resulting precipitate was filtered and washed with water. The reaction product was purified by recrystallisation from a mixture of ethyl acetate and hexane, yielding [1-(4-nitro-phenyl)-piperidin-4-yl]-acetic acid ethyl ester (intermediate 3, mp. 83-85° C.).

b) A mixture of intermediate (3) (0.0055 mol) in THF (50 ml) was hydrogenated with palladium on carbon (10%; 0.16 g) as a catalyst for 30 minutes at a temperature of 50° C. After uptake of hydrogen (1 equivalent), the catalyst was filtered off and the filtrate was evaporated, yielding [1-(4-amino-phenyl)-piperidin-4-yl]-acetic acid ethyl ester (intermediate 4).

Example A.3

Thionyl chloride (3.6 ml) was added to a clear solution of 4'-(trifluoromethyl)-[1,1'-biphenyl]-2-carboxylic acid (0.025 mol) in DMF (1 ml) and DCM (100 ml). The mixture was stirred and refluxed for one hour. The solvent was evaporated. DCM (50 ml) was added to the residue, then evaporated, yielding 4'-(trifluoromethyl)-[1,1'-biphenyl]-2-carbonyl chloride (intermediate 5).

6-Methyl-4'-(trifluoromethyl)-[1,1'-biphenyl]-2-carbonyl chloride (intermediate 6) was prepared analogously starting from 6-methyl-4'-trifluoromethylbiphenyl-2-carboxylic acid using the method as described above.

Example A.4 a) A mixture of Novabiochem 01-64-0261 commercial resin (5 g), benzylamine (1.765 g) and titanium (IV) isopropoxide (4.686 g) in DCM (150 ml) was stirred gently for one hour at room temperature. Sodium triacetoxyborohydride (4.5 g) was added and the reaction mixture was stirred at room temperature for 18 hours. Methanol (10 ml) was added and the mixture was stirred for one hour, then filtered, washed once with DCM, once with methanol, then once with DCM (50 ml)+DIPEA (5 ml), washed three times with firstly DCM, followed secondly by methanol, then dried, yielding 5.23 g of resin (I-a).

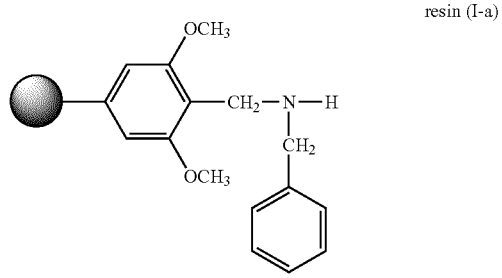

resin (I-a)

b) Piperidine-1,4-dicarboxylic acid mono-(9H-fluoren-9-ylmethyl) ester (Fmoc-isonipecotic acid) (0.3 mmol) was dissolved in a mixture of DCM (2 ml) and DMF (0.5 ml) and added to a mixture of resin (I-a) (150 mg) in DCM (1 ml), followed by addition of TFFH (0.3 mmol) in DCM (0.5 ml) and DIPEA (0.6 mmol) in DCM (0.5 ml). The reaction mixture was shaken for 20 hours at room temperature. The mixture was filtered, washed with DCM (3×), $CH_3OH$ (3×), DCM (3×), $CH_3OH$ (3×), DCM (3×), $CH_3OH$ (3×). A mixture of piperidine in DMF (20%; 3 ml) was added and the reaction mixture was shaken for 3 hours at room temperature. The mixture was filtered, washed with DCM (3×), $CH_3OH$ (3×), DCM (3×), $CH_3OH$ (3×), DCM (3×), $CH_3OH$ (3×), yielding resin (I-b).

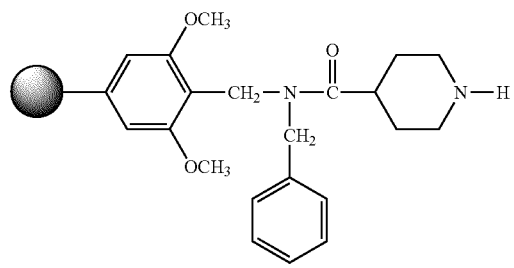

resin (I-b)

c) A mixture of 1-fluoro-4-nitrobenzene (0.5 mmol) in NMP (0.5 ml) was added to resin (I-b) in NMP (3 ml). DIPEA (1 mmol) dissolved in NMP (0.5 ml) was added and the reaction mixture was shaken for 18 hours at a temperature of 50° C. The reaction mixture was cooled, filtered, washed with DCM (3×), $CH_3OH$ (3×), DCM (3×), $CH_3OH$ (3×), DCM (3×), $CH_3OH$ (3×), yielding resin (I-c).

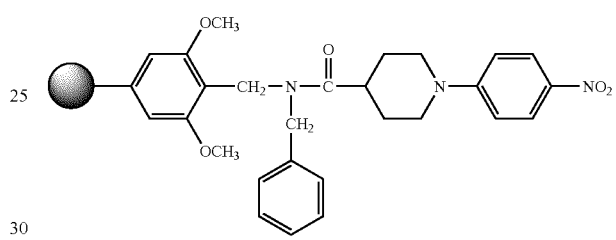

resin (I-c)

d) A mixture of resin (I-c) and tin chloride (2 mmol) in NMP (4 ml) was shaken for 94 hours at a temperature of 50° C. The reaction mixture was cooled, filtered, washed with DCM (3×), $CH_3OH$ (3×), DCM (3×), $CH_3OH$ (3×), DCM (3×), $CH_3OH$ (3×), yielding resin (I-d).

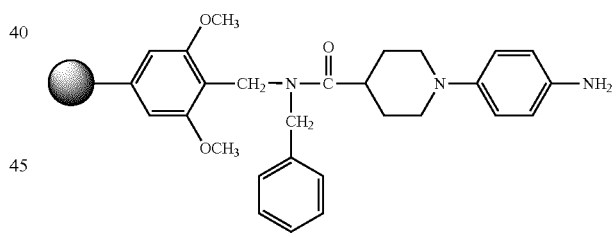

resin (I-d)

Example A.5 a) Sodium nitromalondialdehyde hydrate (0.0143 mol) and S-methylisothiouronium hemisulfate (0.0254 mol) were dissolved in water (40 ml) and piperidin-4-yl-acetic acid ethyl ester (0.0214 mol) (obtained by converting piperidin-4-yl-acetic acid ethyl ester hydrochloride into its free base) was added. The reaction mixture was heated on a water bath for 10 minutes and was left to stand overnight. The resulting precipitate was filtered off and washed with water. The mother layers were treated with $NaHCO_3$ (2 g) and warmed to 60° C. for 10 minutes, then the mixture was cooled and left to stand overnight. Finally, the resulting precipitate was filtered off, yielding [1-(5-nitro-pyrimidin-2-yl)-piperidin-4-yl]-acetic acid ethyl ester (intermediate 7).

b) A solution of intermediate (7) (0.011 mol) in ethyl acetate (100 ml) was hydrogenated at room temperature for 16 hours at atmospheric pressure with palladium-on-carbon (10%, 0.3 g) as a catalyst and hydrogen (3 equivalents). The reaction mixture was filtered over celite and washed with ethyl acetate. The filtrate was evaporated, yielding 1.9 g of [1-(5-amino-pyrimidin-2-yl)-piperidin-4-yl]-acetic acid ethyl ester (intermediate 8).

B. Synthesis of the Final Compounds

Example B.1

A solution of intermediate (6) (0.005 mol) in dioxane (5 ml) was added to a solution of intermediate (2) (0.005 mol) in dioxane (15 ml) and triethylamine (0.005 mol) was added. The reaction mixture was stirred at room temperature for 1 hour and then diluted with water. The reaction product was extracted with ethyl acetate (100 ml) and the organic layer was washed with brine, dried, evaporated, and the resulting oil was then purified by column chromatography silica gel using a mixture of ethyl acetate/hexane (1:4) as eluent, yielding (compound 14, mp. 134-137° C.).

Example B.2

4'-(Trifluoromethyl)-[1,1'-biphenyl]-2-carboxylic acid (0.3 mmol) dissolved in a mixture of DCM and DMF (80:20) (1 ml) was added to resin (I-d) in DCM (1 ml). A solution of TFFH (0.3 mmol) in DCM (1 ml) was added, followed by addition of a solution of DIPEA (0.6 mmol) in DCM (1 ml). The reaction mixture was shaken for 48 hours. The reaction mixture was filtered, washed with DCM (3×), $CH_3OH$ (3×), DCM (3×), $CH_3OH$ (3×), DCM (3×), and $CH_3OH$ (3×). TFA/TIS/DCM (5:2:93) (4 ml) was added and the mixture was shaken for one hour, then filtered. More TFA/TIS/DCM (5:2:93) (2 ml) was added and the reaction mixture was shaken for 15 minutes, then filtered. The filtrates were blown dry under nitrogen at 50° C. The residue was taken up in DCM (3 ml) and treated with an aqueous $Na_2CO_3$ solution. The organic phase was purified by HPLC over Chromasil 5 μm column (20 mm i.d.×150 mm), eluent: 100% DCM to DCM/methanol (90/10 over 15 minutes). The desired fractions were collected and the organic solvent was evaporated, yielding compound (1).

Example B.3

6-Methyl-4'-trifluoromethylbiphenyl-2-carboxylic acid (0.0025 mol) was dissolved in dry DCM (140 ml) together with oxalyl dichloride (2.4 ml) and a few drops of DMF at 0° C. Then, further 6-methyl-4'-trifluoromethylbiphenyl-2-carboxylic acid (0.0225 mol) was added in portions, under a stream of nitrogen gas. The reaction mixture was heated gently to 40° C. until a homogeneous solution resulted and gas evolution had stopped. The mixture was allowed to cool to room temperature, then filtered off over a Buchner filter. The filter residue was dissolved in DCM, then added dropwise at 0° C. to a solution of intermediate (4) (0.025 mol) and triethylamine (3 g) in DCM (140 ml). The reaction mixture was allowed to warm to room temperature over 90 minutes. The precipitate was filtered off, dried and purified by HPLC over Hyperprep C-18, yielding compound (10).

Compound (10) (0.00042 mol) was dissolved in 2-propanol (5 ml) by heating. A solution of HCl (6 M) in 2-propanol (0.00042 mol) was added and the mixture was cooled to room temperature followed by evaporation of the solvent. The residue was crystallized from a mixture of ethanol and DIPE, yielding the hydrochloric acid addition salt of compound (10).

Compound (10) (0.00042 mol) was dissolved in 2-propanol (5 ml) by heating. Methane sulfonic acid (0.00042 mol) was added and the solution was cooled to room temperature. The precipitate was filtered off and dried, yielding the methanesulfonate addition salt of compound (10).

Compound (10) (0.00042 mol) was dissolved in 2-propanol (5 ml) by heating. Maleic acid (0.00042 mol) was added and the solution was cooled to room temperature. The precipitate was filtered off and dried, yielding the maleate addition salt of compound (10).

Example B.4

Compound (16) (0.0014 mol) was suspended in ethanol (5 ml) and $NH_3$ (5 ml) was added and the reaction mixture was stirred and refluxed overnight. The mixture was cooled to room temperature and a precipitate was filtered off. The filtrate was evaporated and purified by flash column chlormatography, yielding compound (17).

Example B.5

4'-Trifluoromethylbiphenyl-2-carboxylic acid (0.0072 mol) in thionyl chloride (2.1 ml) was stirred and refluxed for 3 hours under nitrogen flow. Excess thionyl chloride was evaporated off. Toluene (10 ml) was added to the residue and the mixture was evaporated on the rotary evaporator. The residue was dissolved in DCM (10 ml) and cooled to 0° C. under nitrogen flow. A solution of intermediate (8) and triethylamine (1.1 ml) in DCM (10 ml) was added dropwise. The reaction mixture was slowly warmed to 20° C. then stirring was continued for 16 hours. The solvent was evaporated and the residue was purified by column chromatography over silica gel (eluent:ethyl acetate/hexane 1:1), yielding 2.76 g of compound (16).

Table F-1 lists the compounds that were prepared according to one of the above Examples.

TABLE F-1

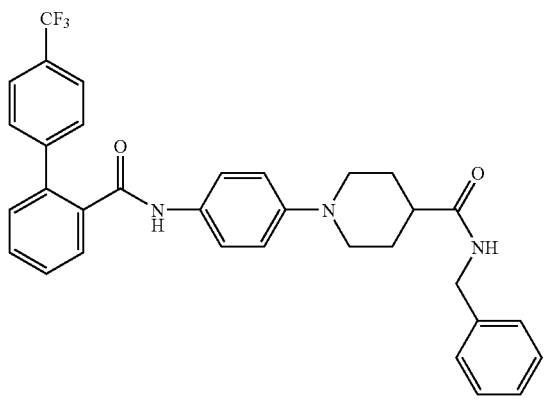

Co. No. 1; Ex. B.2

TABLE F-1-continued
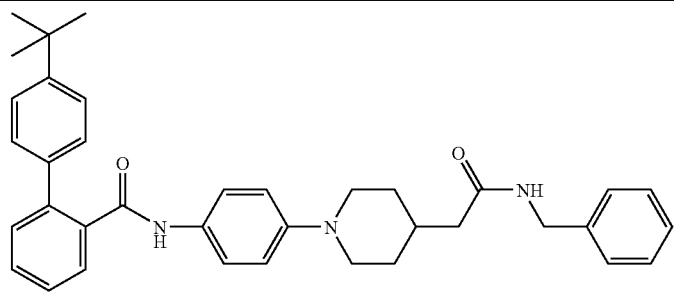
Co. No. 2; Ex. B.2
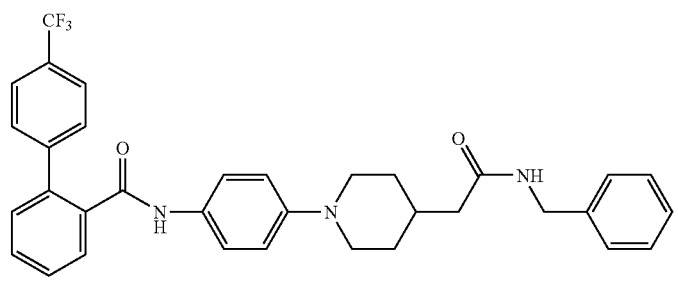
Co. No. 3; Ex. B.2
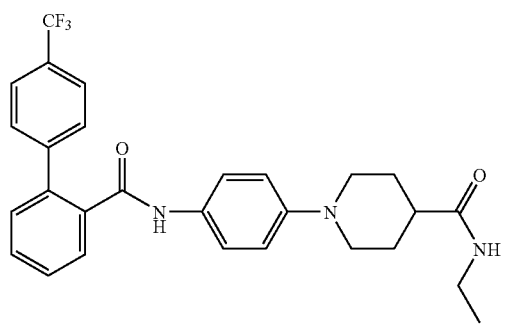
Co. No. 4; Ex. B.2
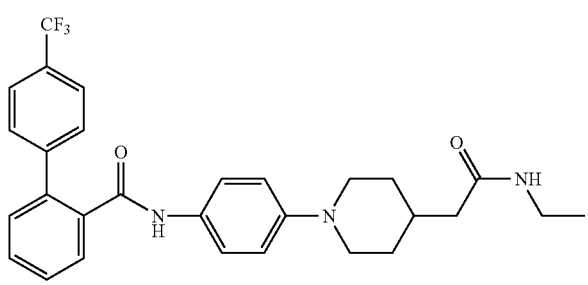
Co. No. 5; Ex. B.2

TABLE F-1-continued
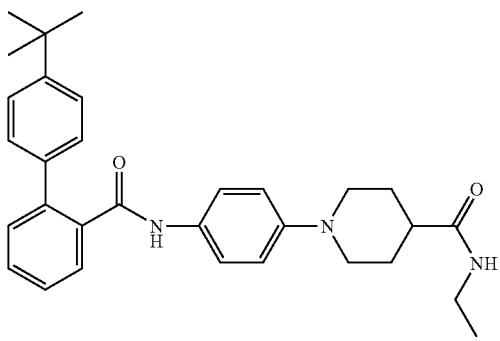
Co. No. 6; Ex. B.2
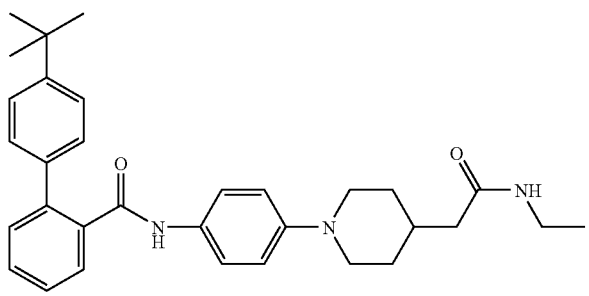
Co. No. 7; Ex. B.2
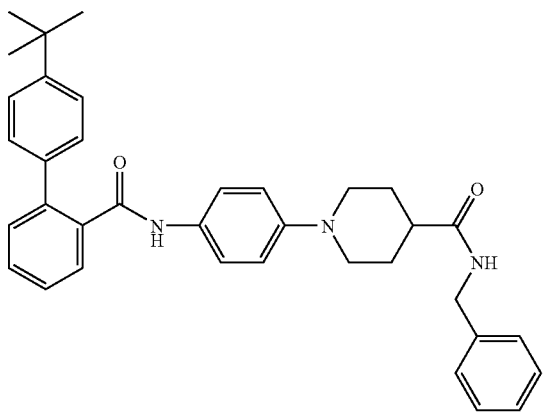
Co. No. 8; Ex. B.2
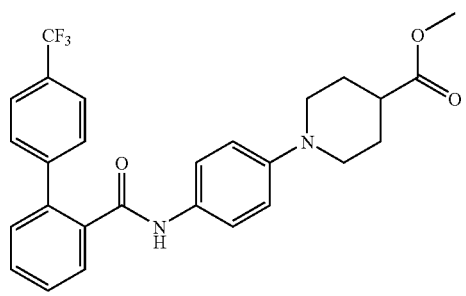
Co. No. 9; Ex. B.1

TABLE F-1-continued
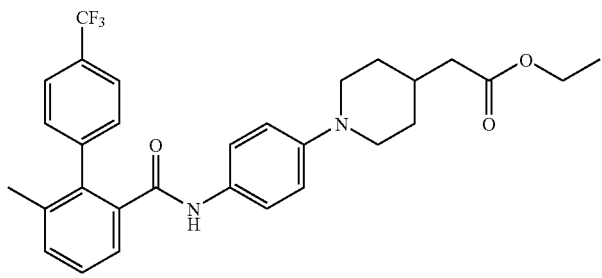
Co. No. 10; Ex. B.3; mp. 153-156° C.
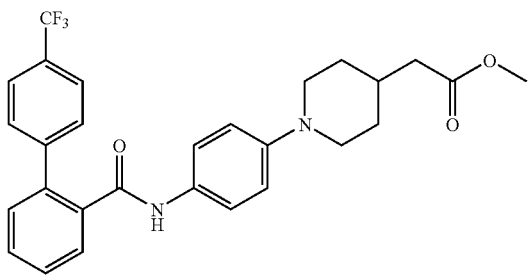
Co. No. 11; Ex. B.1
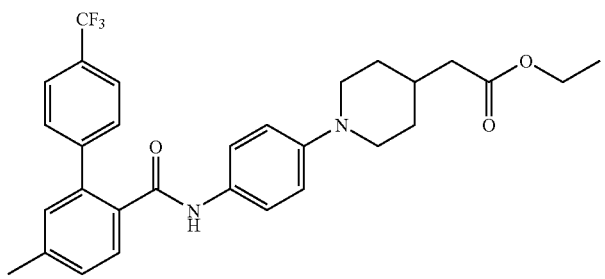
Co. No. 12; Ex. B.1
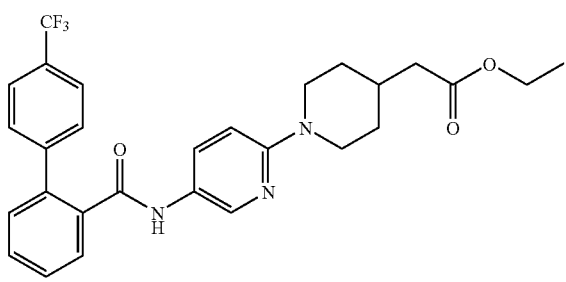
Co. No. 13; Ex. B.1; mp. 155-157° C.
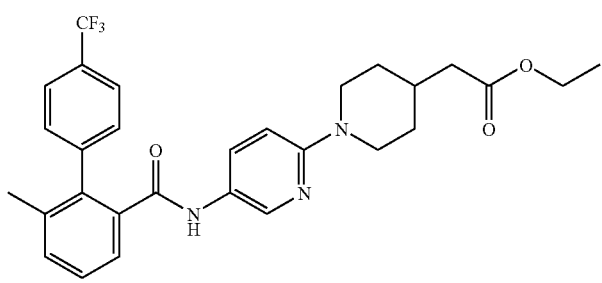
Co. No. 14; Ex. B.1; mp. 134-137° C.

TABLE F-1-continued

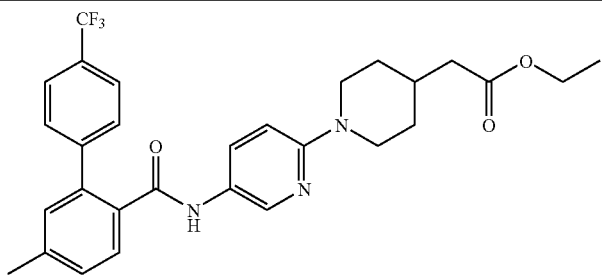

Co. No. 15; Ex. B.1

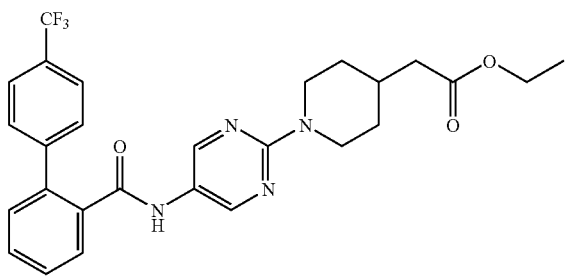

Co. No. 16; Ex. B.5

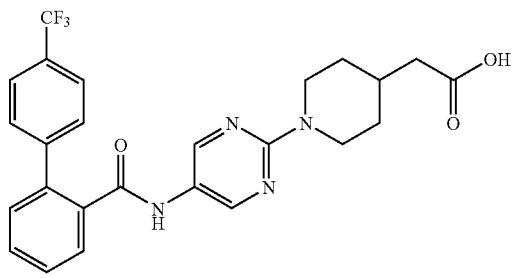

Co. No. 17; Ex. B.4

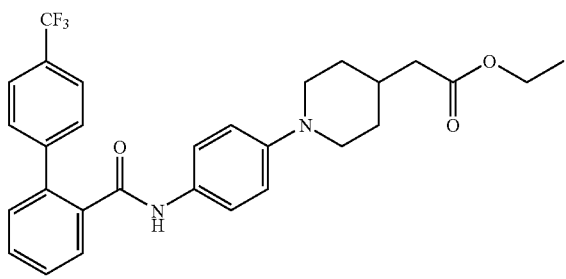

Co. No. 18; Ex. B.1

C. Pharmacological Examples

C1. Quantification of the Secretion of ApoB

HepG2 cells were cultured in 24-well plates in MEM Rega 3 containing 10% fetal calf serum. At 70% confluency, the medium was changed and the test compound or carrier (DMSO, 0.4% final concentration) was added. After 24 hours of incubation, the medium was transferred to Eppendorf tubes and cleared by centrifugation. A sheep antibody directed against either apoB was added to the supernatant and the mixture was kept at 8° C. for 24 hours. Then, rabbit anti-sheep antibody was added and the immune complex was allowed to precipitate for 24 hours at 8° C. The immunoprecipitate was pelleted by centrifugation for 25 minutes at 1320 g and washed twice with a buffer containing 40 mM Mops, 40 mM NaH$_2$PO$_4$, 100 mM NaF, 0.2 mM DTT, 5 mM EDTA, 5 mM EGTA, 1% Triton-X-100, 0.5% sodium deoxycholate (DOC), 0.1% SDS, 0.2 μM leupeptin and 0.2 μM PMSF. Radioactivity in the pellet was quantified by liquid scintillation counting.

Resulting IC$_{50}$ values are enumerated in Table C.1.

TABLE C.1

| Co. No. | pIC50 |
|---|---|
| | pIC50 values (=−log IC$_{50}$ value) |
| 1 | 7.595 |
| 2 | 8.219 |
| 3 | 8.448 |
| 4 | 8.096 |
| 5 | 7.416 |
| 6 | 7.934 |
| 7 | 8.621 |
| 8 | 6.814 |
| 9 | 6.208 |
| 10 | 7.947 |
| 11 | 7.917 |
| 12 | 7.503 |
| 13 | 7.048 |
| 14 | 8.032 |
| 15 | 7.591 |

C.2. MTP Assay

MTP activity was measured using an assay similar to one described by J. R. Wetterau and D. B. Zilversmit in *Chemistry and Physics of Lipids*, 38, 205-222 (1985). To prepare the donor and acceptor vesicles, the appropriate lipids in chloroform were put into a glass test tube and dried under a stream of N$_2$. A buffer containing 15 mM Tris-HCl pH 7.5, 1 mM EDTA, 40 mM NaCl, 0.02% NaN$_3$ (assay buffer) was added to the dried lipid. The mixture was vortexed briefly and the lipids were then allowed to hydrate for 20 min on ice. Vesicles were then prepared by bath sonication (Branson 2200) at room temperature for maximum 15 min. Butylated hydroxytoluene was included in all vesicle preparations at a concentration of 0.1%. The lipid transfer assay mixture contained donor vesicles (40 nmol phosphatidylcholine, 7.5 mol % of cardiolipin and 0.25 mol % glycerol tri [1-$^{14}$C]-oleate), acceptor vesicles (240 nmol phosphatidylcholine) and 5 mg BSA in a total volume of 675 μl in a 1.5 ml microcentrifuge tube. Test compounds were added dissolved in DMSO (0.13% final concentration). After 5 minutes of pre-incubation at 37° C., the reaction was started by the addition of MTP in 100 μl dialysis buffer. The reaction was stopped by the addition of 400 μl DEAE-52 cellulose pre-equilibrated in 15 mM Tris-HCl pH 7.5, 1 mM EDTA, 0.02% NaN$_3$ (1:1, vol/vol). The mixture was agitated for 4 min and centrifuged for 2 min at maximum speed in an Eppendorf centrifuge (4° C.) to pellet the DEAE-52-bound donor vesicles. An aliquot of the supernatant containing the acceptor liposomes was counted and the [$^{14}$C]-counts were used to calculate the percent triglyceride transfer from donor to acceptor vesicles.

The invention claimed is:

1. A compound of formula (I)

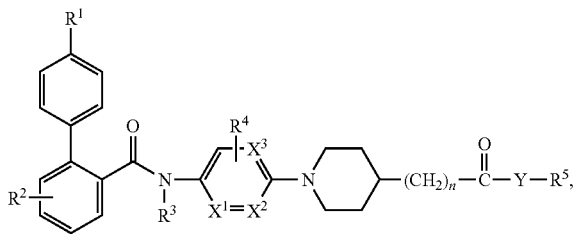

(I)

the N-oxides, the pharmaceutically acceptable acid addition salts and the stereochemically isomeric forms thereof, wherein
R$^1$ is hydrogen, C$_{1-4}$alkyl, halo, or polyhaloC$_{1-4}$alkyl;
R$^2$ is hydrogen, C$_{1-4}$alkyl, halo, or polyhaloC$_{1-4}$alkyl;
R$^3$ is hydrogen or C$_{1-4}$alkyl;
R$^4$ is hydrogen, C$_{1-4}$alkyl, or halo;
n is an integer zero or 1;
X$^1$ and X$^2$ are either both carbon, X$^1$ is carbon and X$^2$ is nitrogen, or X$^1$ is nitrogen and X$^2$ is carbon;
X$^3$ is carbon, or nitrogen provided that only one of X$^1$ or X$^2$ is nitrogen;
Y is O or NR$^6$ wherein R$^6$ is hydrogen or C$_{1-4}$alkyl; and
R$^5$ is C$_{1-4}$alkyl or C$_{1-4}$alkyl substituted with phenyl.

2. A compound as claimed in claim 1 wherein X$^1$, X$^2$ and X$^3$ are carbon.

3. A compound as claimed in claim 1 wherein X$^1$ is carbon, X$^2$ is nitrogen, and X$^3$ is carbon.

4. A compound as claimed in claim 1 wherein X$^1$ is nitrogen, X$^2$ is carbon, and X$^3$ is carbon.

5. A compound as claimed in claim 1 wherein n is the integer zero.

6. A compound as claimed in claim 1 wherein n is the integer 1.

7. A pharmaceutical composition comprising a pharmaceutically acceptable carrier and a therapeutically active amount of a compound as claimed in claim 1.

8. A process for preparing a pharmaceutical composition as claimed in claim 7 wherein a therapeutically active amount of a compound of formula (I) is intimately mixed with a pharmaceutically acceptable carrier.

9. A process for preparing a compound of formula (I) wherein
an intermediate of formula (II), wherein R$^3$, R$^4$, R$^5$, n, Y, X$^1$, X$^2$ and X$^3$ are defined as in claim 1,

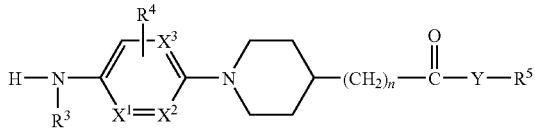

(II)

is reacted with a biphenylcarboxylic acid or halide having the formula (III), wherein R$^1$ and R$^2$ are as defined in formula (I) and Q$^1$ is selected from hydroxy and halo, in at least one reaction-inert solvent and optionally in the presence of a suitable base

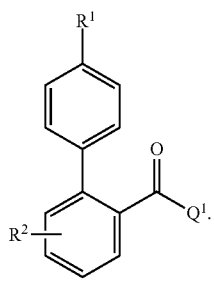
(III)

10. The method according to claim 9 further comprising converting the compound of formula (I) into an acid addition salt.

11. A compound as claimed in claim 2 wherein n is the integer zero.

12. A compound as claimed in claim 3 wherein n is the integer zero.

13. A compound as claimed in claim 4 wherein n is the integer zero.

14. A compound as claimed in claim 2 wherein n is the integer 1.

15. A compound as claimed in claim 3 wherein n is the integer 1.

16. A compound as claimed in claim 4 wherein n is the integer 1.

17. A method of treating a warm-blooded animal suffering from a disorder which is hyperlipidemia, obesity, atherosclerosis or type II diabetes comprising administering to the animal suffering from such disorder a therapeutically effective amount of a compound of claim 1.

* * * * *